(12) United States Patent
Wilson et al.

(10) Patent No.: US 6,638,266 B2
(45) Date of Patent: Oct. 28, 2003

(54) GUIDEWIRE WITH AN INTERMEDIATE VARIABLE STIFFNESS SECTION

(75) Inventors: W. Stan Wilson, Missoula, MT (US); Robert C. Esselstein, Fallbrook, CA (US); Wayne E. Cornish, Fallbrook, CA (US); Mark T. Richardson, Escondido, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 10/310,392

(22) Filed: Dec. 5, 2002

(65) Prior Publication Data

US 2003/0083643 A1 May 1, 2003

Related U.S. Application Data

(63) Continuation of application No. 09/748,294, filed on Dec. 21, 2000, now Pat. No. 6,524,301.

(51) Int. Cl.[7] .............................................. A61M 25/00
(52) U.S. Cl. ......................................... 604/523; 604/531
(58) Field of Search .................................. 604/523, 531, 604/164.13, 164.12, 164.01; 600/585, 434

(56) References Cited

U.S. PATENT DOCUMENTS

| | | | |
|---|---|---|---|
| 4,538,622 A | 9/1985 | Samson et al. | |
| 4,748,986 A | 6/1988 | Morrison et al. | |
| 5,007,434 A | * 4/1991 | Doyle et al. ................ | 600/585 |
| 5,061,395 A | 10/1991 | Meng | |
| 5,135,503 A | 8/1992 | Abrams | |
| 5,341,818 A | 8/1994 | Abrams et al. | |
| 5,345,945 A | 9/1994 | Hodgson et al. | |
| 5,497,785 A | * 3/1996 | Viera .......................... | 600/585 |
| 5,507,301 A | 4/1996 | Wasicek et al. | |
| 5,507,729 A | * 4/1996 | Lindenberg et al. .... | 604/170.01 |
| 5,902,254 A | * 5/1999 | Magram ..................... | 600/585 |
| 5,931,819 A | 8/1999 | Fariabi | |
| 6,106,485 A | 8/2000 | McMahon | |
| 6,106,488 A | 8/2000 | Fleming et al. | |
| 6,142,958 A | 11/2000 | Hammarstrom et al. | |
| 6,296,616 B1 | 10/2001 | McMahon | |
| 6,524,301 B1 | * 2/2003 | Wilson et al. ............... | 604/523 |

* cited by examiner

*Primary Examiner*—Henry C. Yuen
*Assistant Examiner*—Hyder Ali
(74) *Attorney, Agent, or Firm*—Fulwider Patton Lee & Utecht, LLP

(57) ABSTRACT

The invention is directed to an guide wire for intraluminal deployment of a medical device within a patient, the guide wire having an elongate core member with an intermediate core section comprising a plurality of contiguous segments in alignment with the longitudinal axis of the core member with alternating flexible and rigid core segments, so that the articulated section bends in a discontinuous, discrete manner when advanced through a curved blood vessel or other body lumen within the patient. When an obstruction on a vessel wall causes the catheter or other coaxial device to be impeded, the guide wire and intermediate core section may alternately be advanced and retracted a short distance through the catheter distal tip causing a "nodding" motion of the catheter tip while the catheter is pushed through the vessel, so as to avoid and bypass the vessel obstruction.

12 Claims, 3 Drawing Sheets

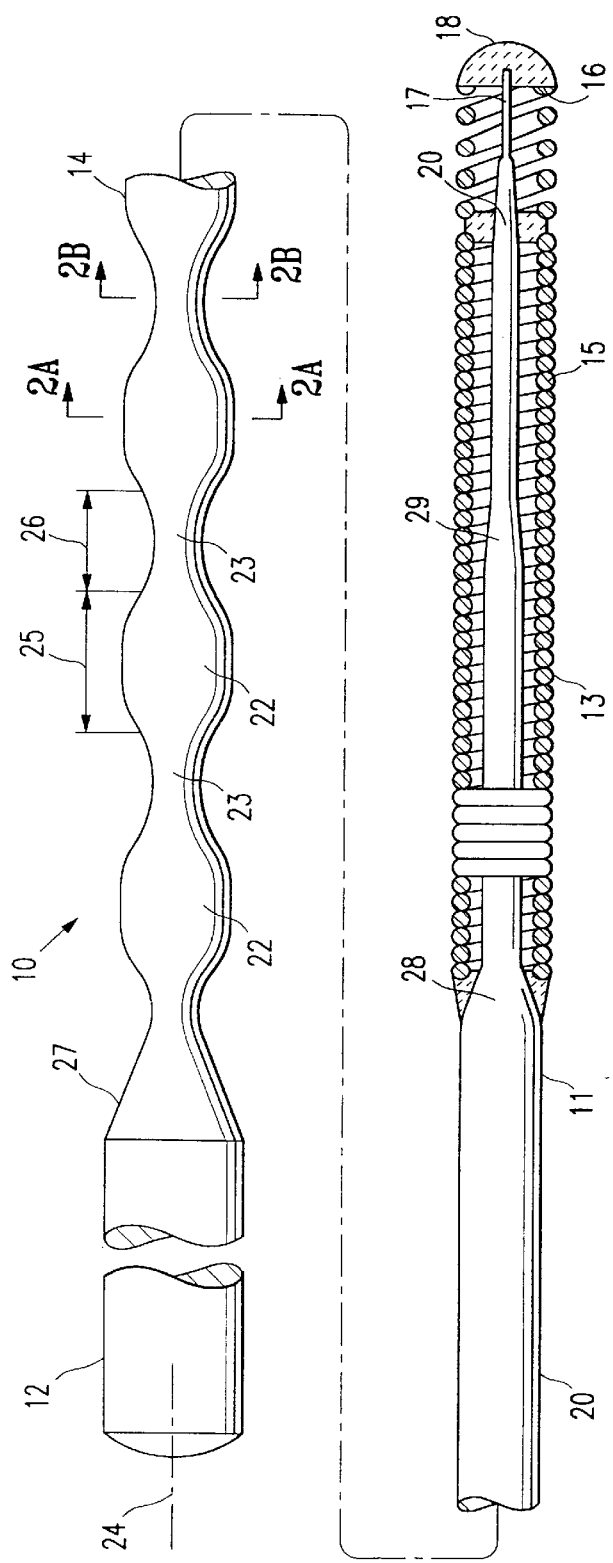
FIG. 1
FIG. 2A
FIG. 2B

GUIDEWIRE WITH AN INTERMEDIATE VARIABLE STIFFNESS SECTION

CROSS REFERENCE TO RELATED APPLICATIONS

This is a continuation application of parent application having U.S. Ser. No. 09/748,294 filed Dec. 21, 2000 now U.S. Pat. No. 6,524,301, the contents of which is hereby incorporated by reference.

BACKGROUND OF THE INVENTION

This invention relates to the field of intraluminal guide wires for advancing catheters such as stent delivery catheters, balloon dilatation catheters, atherectomy catheters and the like, within body lumens.

In a typical percutaneous coronary procedure, a guiding catheter having a preformed distal tip is percutaneously introduced into a patient's peripheral artery, e.g. femoral or brachial artery, by means of a conventional Seldinger technique and advanced therein until the distal tip of the guiding catheter is seated in the ostium of a desired coronary artery. For rapid exchange type catheters having a short guidewire receiving lumen within their distal extremities, a guide wire is first advanced by itself through the guiding catheter until the distal tip of the guide wire extends beyond the arterial location where the procedure is to be performed. Then a rapid exchange type catheter, such as described in U.S. Pat. No. 5,061,395 (Yock), is mounted onto the proximal portion of the guide wire which extends out of the proximal end of the guiding catheter which extends outside of the patient. Over the wire type catheters (OTW) have guidewire lumens which extend through the entire length of the catheter and with these types of catheters the guidewire and OTW catheters are advanced together within the guiding catheter until the distal ends thereof are at the distal end of the guiding catheter. The guidewire is then advanced out the distal I end of the guiding catheter into the body lumen until the distal end of the guidewire is disposed beyond the procedure site.

In either case, once the guidewire is in place with the distal end distal to the procedure site, the intravascular catheter is then advanced over the guide wire, while the position of the guide wire is fixed, until the operative means on the catheter is disposed within the arterial location where the procedure is to be performed. After the procedure, the intravascular catheter may be withdrawn from the patient or the guide wire repositioned within the coronary anatomy for an additional procedure.

Further details of guide wires, and devices associated therewith for various interventional procedures can be found in U.S. Pat. No. 4,748,986 (Morrison et al.); U.S. Pat. No. 4,538,622 (Samson et al.); U.S. Pat. No. 5,135,503 (Abrams); U.S. Pat. No. 5,341,818 (Abrams et al.); and U.S. Pat. No. 5,345,945 (Hodgson, et al.) which are hereby incorporated herein in their entirety by reference thereto.

Conventional guide wires for angioplasty, stent delivery, atherectomy and other intravascular procedures usually have an elongate core member with relatively stiff proximal section and a flexible distal section with one or more distally tapered segments. A flexible body member, such as a helical coil or a tubular body of polymeric material, is typically disposed about the distal section of the core member. A shapeable member, which may be the distal extremity of the core member or a separate shapeable ribbon which is secured to the distal extremity of the core member extends through the flexible body and is secured to the distal end of the flexible body by soldering, brazing or welding, or an adhesive in the case of polymeric flexible bodies which forms a rounded distal tip. The distal section is flexible and will not damage or perforate the vessel or body lumen through which it is advanced and the portion behind the distal tip is increasingly stiff which better supports a balloon catheter or similar device.

The advancement of an intraluminal catheter over a guide wire may be difficult where intravascular tortuosity, calcification, noncompliance, fibrotic plaque, previously deployed stents or other obstructions are present proximal to the target site or lesion. With the use of conventional guide wires having a core member of longitudinally constant stiffness in their proximal sections, the contact of the guidewire with vessel walls, e.g., adjacent a bend in the vessel, may cause the advancing catheter or other device to impinge or "catch" upon such an obstruction, impeding advancement.

The use of a guide wire of lower stiffness may lessen the friction force of the catheter upon the vessel wall and obstruction, but the reduced stiffness may lead to insufficient "pushability" and prolapse of the guide wire.

One useful approach to easing advancement of the catheter through proximal obstructions is the use of a guidewire commonly called a "wiggle wire" which has a core length that is formed into a plurality of "kinks" or undulations where the core length has an S-shape. See for example U.S. Pat. No. 5,007,434 (Doyle et al.) assigned to the present assignee which is incorporated by reference herein in its entirety. When an obstruction is encountered, the portion of the "wiggle wire" guidewire having the undulating or S-shaped core segment is alternately advanced and retracted through the catheter distal tip, causing the tip to "nod" laterally from side-to-side while the catheter is pushed through the vessel, so as to avoid and bypass the obstruction on the vessel wall. However, the guidewire with the kinked or undulating shape generally results in reduced steerability and control for the guidewire, and may require a larger guidewire lumen in the catheter to accommodate the undulated shape which increases the catheter profile.

SUMMARY OF INVENTION

The present invention is directed to an guide wire for the deployment of an elongated medical device within a patient's body lumen. The guidewire includes an elongated core member with a proximal core section, a distal core section more flexible than the proximal core section and a flexible body such as a coil or polymeric tube disposed about and secured to the distal core section. The core member includes an intermediate core section disposed between the proximal core section and the distal core section, which has a plurality of segments or sub-portions which alternate between relatively stiff and relatively flexible contiguous segments or sub-portions along a length of the intermediate core section. A flexible segment between two adjacent stiff segments allow the intermediate core section to articulate when advancing through a tortuous body lumen so that the intermediate section bends discontinuously into discrete portions.

The segments of the intermediate core section are disposed in a linear arrangement and alternate between being relatively rigid or stiff and being relatively non-rigid or flexible, along a significant length of the intermediate core section. Thus, each flexible segment is bounded on each end by a stiff segment to allow articulation between the two stiff segments. When the intermediate core section of the guide wire is advanced into a curved portion or bend in the vessel, the intermediate section as a whole bends to conform overall with the vessel curvature. The flexible intermediate segments are substantially less resistant to bending than the stiff intermediate segments; so as a result most of the bending occurs in the flexible core segments, with the relatively stiff intermediate segments remaining relatively straight or otherwise undeformed and articulating about the flexible segments.

When a catheter is advanced through a body lumen over a conventional guidewire and the leading edge of the catheter engages an obstruction in the wall of the vessel, such as a strut from a previously deployed stent, a ledge of fibrotic plaque, or the like, further advancement of the catheter is impeded. However, utilization of a guide wire having features of the invention will allow the distal tip of the catheter to oscillate or nod. The oscillation or "nod" motion of the catheter's distal tip causes the distal tip to periodically reduce or eliminate contact with the obstruction while the catheter is pushed through the vessel. To provide the oscillation of the catheter's distal tip, the intermediate core section lies adjacent and across the obstruction. Either the catheter or the guide wire, or both, may be moved longitudinally to an advanced or a retracted position a sufficient distance so that the distal tip of the catheter has alternating contact with bent flexible intermediate segments and straight stiff intermediate segments which causes the catheter tip to "nod" laterally from side-to-side. The distal tip of the catheter should oscillate or nod a distance of about 0.1 to about 3 mm, preferably about 0.5 to about 1 mm, in order to avoid or bypass the vessel obstruction.

The intermediate core section of the guidewire should have at least one flexible intermediate core segment with proximally and distally adjacent stiff intermediate core sections so that there is at least one point, preferably about 3 to about 5 points or regions of articulation in the bending of the guide wire between the proximal core section and the distal core section. Usually, not more than about 10 points or regions of articulation are needed. The intermediate core section preferably has multiple adjacent pairs of flexible and stiff intermediate core segments to provide an intermediate core section of sufficient length for convenient manipulation by the physician or other operator as the section is alternately advanced and retracted as described above.

The alternating stiff and flexible characteristics can be provided to the intermediate core segments by dimensional changes or material property changes along the length of the intermediate core section. Dimensional changes to produce a periodically variable stiffness characteristic along the length may be made by centerless grinding or otherwise shaping a selected length of the intermediate core section, or adding bands or sheaths to regions of the core, so as to have a periodically variable stiffness along the core. For a core member of substantially circular cross section, the cross-section of the intermediate section may also be circular, with the radius of the cross section being variable longitudinally along a substantial length of the intermediate core section. The rigidity to bending of both the flexible core segments and stiff segments may be determined by selecting a cross section for each based on material mechanical properties.

The transition of cross-sectional variations along the intermediate core section between the stiff and flexible segments is preferably smooth. For example, the radius of the cross section may vary longitudinally in an undulating pattern, e.g. approximately sinusoidal, so that the intermediate core section has a longitudinal surface contour that is undulating. As the intermediate core section is bent to conform to the curvature of a vessel, the inside surface contour (the contour facing the inside of the bend or curve) will have a curvature which is determined both by the variation in diameter of the core within the intermediate section and by the variable curvature of the axis of the intermediate section.

The alternating sections may be of a range of selected overall lengths, typically from about 0.5 to about 10 cm, preferably about 1 to about 5 cm. The pitch or spacing between like segments, i.e. flexible or stiff segments, may range from about 0.1 to about 10 cm. preferably about 1 to about 2 cm. The lengths and transverse dimensions of the intermediate core segments need not be the same along the length of the intermediate core sections. These dimension may be adjusted to provide the desired variations in stiffness along the length of the intermediate section.

The ratio of the rigidity of the stiff segments relative to the flexible segments is substantially greater than unity, e.g. 1.1 to about 1.7, preferably about 1.3 to about 1.5, and is selected to provide a substantial longitudinal variation in curvature of the intermediate core section, when bent to conform to vessel curvature prevailing in vessels in which it is to be used. For a guidewire in which the variation in stiffness in the intermediate section is due to variations in the diameter of the segments having a circular cross section, and wherein the alternating variation in stiffness from segment to segment is due to variation in cross section diameter as described above, the ratio of the maximum diameter of the stiff intermediate segment to the minimum diameter of the flexible intermediate segment is about 5% to about 75%, preferably about 10% to about 20%. A typical example would be the stiff segment having a maximum diameter of about 0.01 inch (0.25 mm) with an adjacent flexible segment having a diameter of about 0.0075 inch (0.19 mm).

Alternatively, the variation in stiffness of the intermediate section may be provided by longitudinal variation in material properties (e.g., by variable heat treatment or by a variation of materials), or by a combination of variation in cross section and variation in material properties.

BRIEF DESCRIPTION OF THE DRAWINGS

FIG. 1 is an elevational view, partially in section, of a guide wire having features of the invention.

FIGS. 2A and 2B are transverse cross-sectional views of the intermediate core section of the guidewire shown in FIG. 1 taken along lines 2A—2A and 2B—2B respectively.

DETAILED DESCRIPTION OF THE INVENTION

Figure 3:
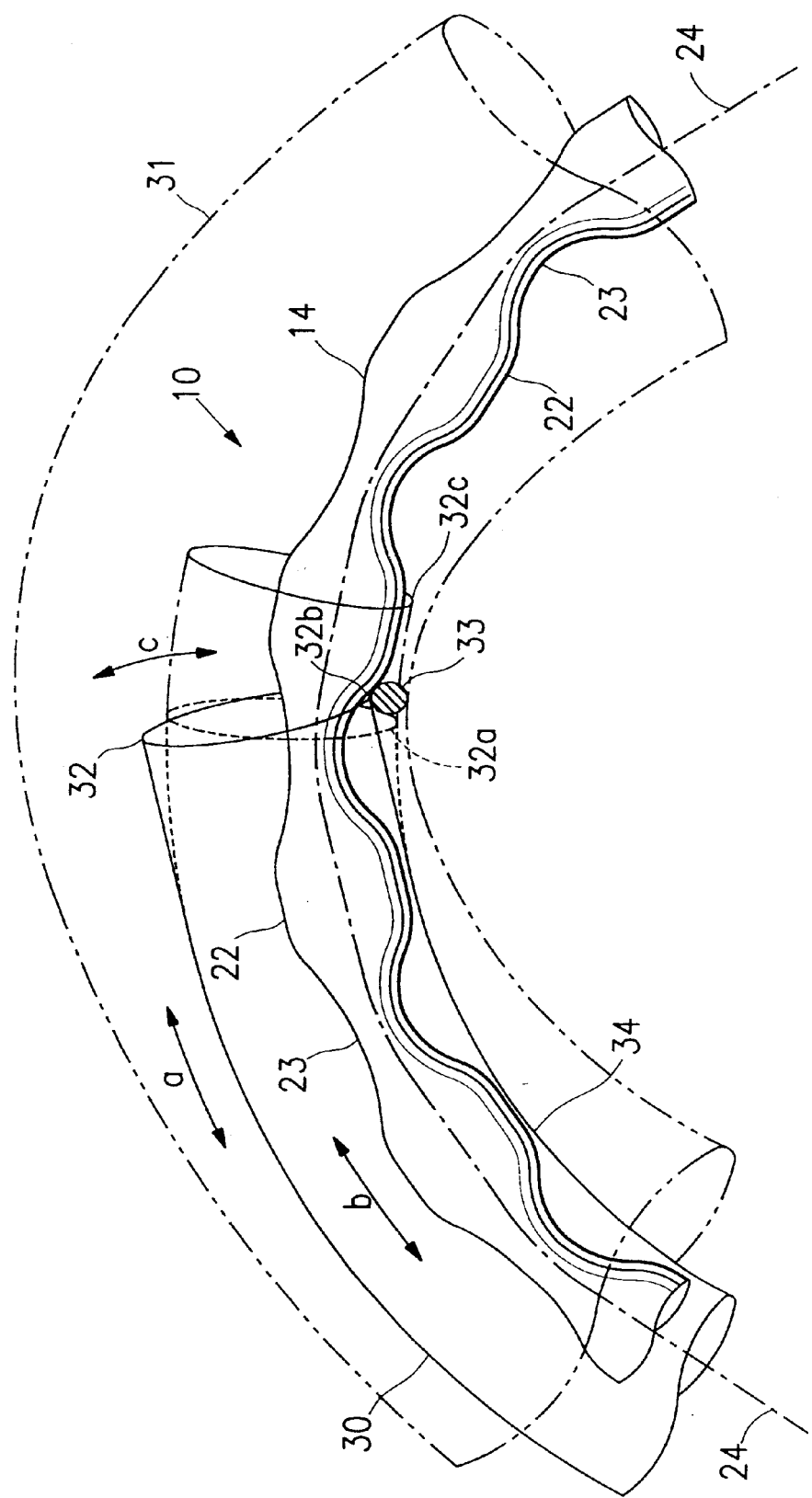
FIG. 3 depicts a catheter being advanced over a guide wire having the intermediate core section shown in FIG. 1, through a bend of a blood vessel and bypassing an obstruction adhered to the vessel wall.

FIG. 1 shows an embodiment of guide wire 10 having features of the invention. The guidewire 10 has an elongated core member 11, a proximal core section 12, a distal core section 13, an intermediate core section 14 which has a variable rigidity and a flexible body or coil 15 disposed about and secured to the distal core section 13. The distal end 16 of the coil 15 is secured to the distal end 17 of the core 11 by weld or solder to form the rounded plug 18. The coil 15 is also secured to the distal core section 13 by weld or solder at an intermediate location 20 and at its proximal end 21.

The intermediate core section 14 has a plurality of relatively-rigid or stiff intermediate core segments 22 and a plurality of relatively flexible intermediate core segments 23. As shown in FIG. 2A, the stiff intermediate core segments 22 have a diameter d1, whereas, as shown in FIG. 2B the flexible intermediate core segments 23 have a diameter d2 which is much smaller than the diameter d1. The intermediate core segments 22 and 23 alternate along a length of the intermediate core section 14 and are joined end-to-end along the longitudinal axis 24 of the guide wire 10. The alternating stiff intermediate core segments 22 and the flexible intermediate core segments 23 have selected lengths 25 and 26 respectively which typically range from about 0.5 to about 10 cm, preferably about 1 to about 5 cm. The exterior contours of the intermediate core segments 22 and 23 smoothly transition between d1 and d2 to provide an undulating shape to the exterior of the intermediate core section 14. The intermediate core section 14 may be covered with a helical coil or plastic layer (not shown) which would have an outer diameter essentially the same as the outer diameter of the proximal core section 12. The core 11 is provided with a tapered junction 27 between proximal section 12 and the intermediate section 14. The distal core section 13 may have one or more tapered sections 28 and 29.

FIG. 3 depicts the intermediate core section 14 shown in FIG. 1 extending across the distal end of a catheter 30 which has been bent to conform to a curved vessel 31 shown in broken line. The leading distal edge 32 of the catheter 30 is shown in broken line as engaging an idealized obstruction or impediment 33. As a result of variable rigidity of the intermediate section 14, the guide wire axis 24 is not bent in a continuous uniform manner, but rather in discrete portions. Thus, the longitudinal axis 24 is essentially straight through the stiff segments 22 and bent in the flexible segments 23 to provide a discontinuous curvature as shown.

In FIG. 3 the catheter 30 is shown being advanced distally over guidewire 10 in the direction of Arrow A through a bend of vessel 31. The intermediate core section 14 of guidewire 10 is shown extending across the distal end of catheter 30 and out into the body lumen 31. As the catheter 30 is advanced, it conforms by contact to the inner contour of the guide wire 10. Note that inner contour 34 of catheter 30 has non-uniform contact with the surface of the intermediate core section 14 of guidewire 10, as the stiff intermediate core segments 22 tend to contact the interior surface of catheter 30 while the flexible intermediate core segments 23 tend to either not contact the inner surface of catheter 30 or contact it with less pressure. As a result, the leading distal edge 32 of catheter 30 intermittently curves and straightens laterally in the direction of Arrow C as the catheter 30 is advanced ("tip nodding").

In the example shown, the position of the obstruction 33 is presumed to be initially in contact with a stiff intermediate core segments 22, causing the distal edge 32 of catheter 30 to contact and become impeded or "stuck" at tip/obstruction contact point as shown in broken line.

However, when the guidewire intermediate section 14 is cyclically advanced and/or retracted as shown by Arrow B, the intermittent contact with the catheter 30 causes the distal tip 32 thereof to intermittently curve and straighten laterally, i.e. oscillate in the direction of Arrow C. Thus the cyclical motion of the intermediate core section 14 as shown by Arrow B produces a "tip nodding" motion even while the catheter 30 is in a static longitudinal position, cycling between lowered tip position 32a and raised distal tip position 32b, as shown by Arrow C. Thus, when the catheter 30 is pushed in the direction of Arrow A simultaneously with the cyclical motion of intermediate section 14 as shown by Arrow B, the resultant "tip nodding" motion permits the distal end 32 of catheter 30 to bypass over the obstruction 33 and advance beyond it to tip position 32c shown in phantom.

The guide wire 10 has other than the intermediate core section 14, a construction generally similar to conventional guide wires. The overall guide wire length may range from about 100 cm to about 330 cm and typically about 170 to 190 cm. The guide wire distal segment includes a helical coil 15, but this may be replaced with a polymer jacket, or the like, which surrounds and covers at least a portion of the distal core section 13. The distal core section 13 is shown as extending to the distal end of the guidewire, but a separate shaping ribbon may be used which extends from the distal end of the core member to the distal end of the guidewire in a conventional fashion. The guide wire may be of conventional materials, such as stainless steel, high strength precipitation hardened cobalt-chromium or cobalt-chromium-molybdenum alloys such as MP35N, Elgiloy and the like or a superelastic NiTi alloy with an $A_f$ at or less than body temperature. The proximal shaft section 12 may be formed of a material different than the distal segmented shaft. The proximal core section of the guide wire core may have a diameter from about 0.007 to 0.035 inch (0.18–0.89 mm), preferably about 0.01 to about 0.014 inch (0.25–0.36 mm) for coronary uses.

Figure 4:
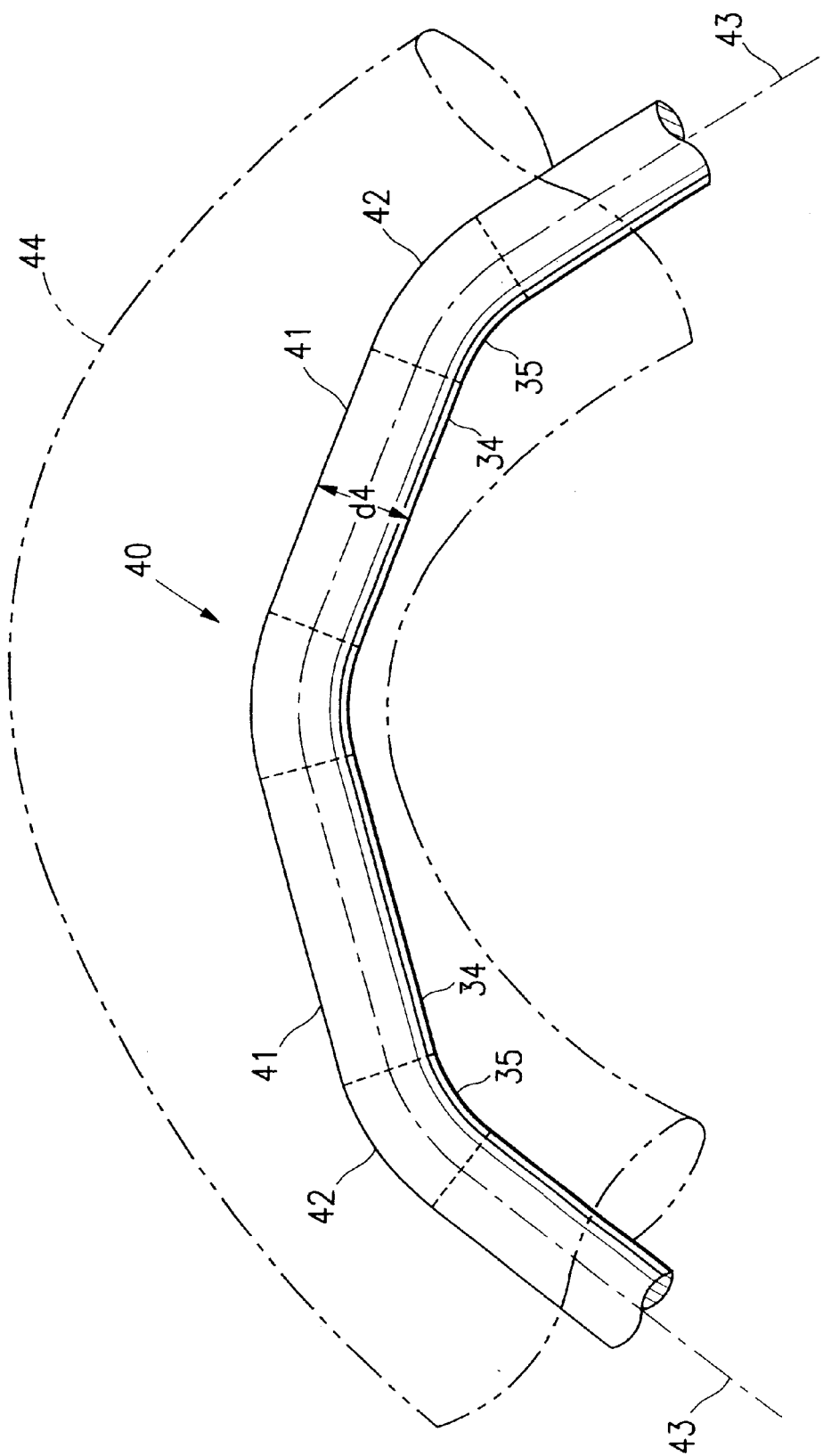
FIG. 4 illustrates an alternative intermediate core section of a guidewire core member embodying features of the invention.

FIG. 4 depicts an alternative embodiment of an intermediate core section 40 suitable for use with a guidewire as described above. In this embodiment, the intermediate core section 40 comprises a plurality of alternating stiff core segments 41 and flexible segments 42. As in the embodiment of FIG. 1, the core segments 41 and 42 are joined end-to-end disposed along the guide wire axis 43. In the embodiment 40, the diameter d4 is uniform along a substantial length of the core section 40. The reduced rigidity of the flexible core segments 42 relative to the stiff segments 41 is due to differing mechanical properties of the material from which these segments are composed, i.e., the stiff core segments 41 can be formed of a relatively rigid material, while the flexible core segments 42 may be formed of a relatively non-rigid material. The material compositions 34 and 35 may comprise the same original material which has been altered discontinuously along the length of the intermediate core section 40 in such a way a to produce the desired variable rigidity, such as by intermittently heat-treating, cross-linking irradiation, absorption of additives, variable depletion of substances, and the like, along the length of intermediate core section 40. Optionally, the material compositions of the segments 41 and 42 may be different materials with inherently differing mechanical properties, with the segments bonded or otherwise joined at the segment junctions.

As the intermediate core section 40 is bent to conform to a curved vessel 44 (shown in phantom), the longitudinal axis 43 through the stiff segments 41 is bent little or negligibly, while the longitudinal axis through the flexible core segments 42 is bent with a greater curvature. This causes the intermediate core section 40 to bend in a discontinuous or intermittent manner as described in the embodiment shown in FIG. 1.

While the above embodiments have been described in terms of dimensional or compositional changes to affect the mechanical properties of the relatively stiff or the relative flexible intermediate core segments, those skilled in the art will recognize that both dimensional and compositional changes may be used to affect the desired variation in mechanical properties in the intermediate core section.

Other methods for affecting a change in properties from core segment to core segment would include providing stiffening sheaths along the intermediate core section. Other methods include having a braided core member with the angle and pattern of the braid being modified to impart the alternating stiffness. Moreover, various modification and improvements may be made to the invention without departing from the scope thereof. Terms such as element, member, device, section, segment and words of similar import when used herein shall not be construed as invoking the provisions of 35 U.S.C. §112(6) unless the following claims expressly use the term "means" or "step" followed by a particular function.

What is claimed is:

1. An intraluminal guidewire, comprising:
   a proximal core section, a distal core section, and an intermediate core section disposed between the proximal core section and the distal core section;
   the intermediate core section includes a plurality of intermediate core segments having substantially the same diameter and having means for creating alternating relatively stiff core segments adjacent relatively flexible core segments; and
   wherein the means for creating relatively stiff core segments and relatively flexible core segments includes at least one of forming the plurality of intermediate core segments at the same material which is altered discontinuously along the length and forming the plurality of intermediate core segments of different materials having differing mechanical properties.

2. The intraluminal guidewire of claim 1, wherein the means for creating further includes alternating cross-sectional areas for the relatively stiff core segments and the relatively flexible core segments.

3. The intraluminal guidewire of claim 1, wherein the means for creating further includes alternating lengths of the relatively stiff core segments and the relatively flexible core segments.

4. The intraluminal guidewire of claim 1, wherein the means for creating further includes alternating the bending rigidity of a material forming the relatively stiff core segments and the relatively flexible cart segments.

5. The intraluminal guidewire of claim 1, wherein the means for creating further includes intermittently heat-treating along the length of the intermediate core section.

6. The intraluminal guidewire of claim 1, wherein the means for creating further includes cross-linking radiation along the length of the intermediate core section.

7. The intraluminal guidewire of claim 1, wherein the means for creating further includes absorption of additives along the length of the intermediate core section.

8. The intraluminal guidewire of claim 1, wherein the means for creating further includes variable depletion of substances along the length of the intermediate core section.

9. An intraluminal guidewire, comprising:
   a proximal core section, a distal core section, and an intermediate core section disposed between the proximal core section and the distal core section;
   wherein the intermediate core section includes an undulating surface contour formed from a plurality of intermediate core segments at least one of which is relatively stiff and an adjacent one is relatively flexible in bending rigidity, wherein the relatively flexible intermediate core segment is formed of a material less rigid than a material forming the relatively stiff intermediate core segment.

10. The intraluminal guidewire of claim 9, wherein the relatively flexible intermediate core segment and the relatively stilt intermediate core segment are spaced apart in periodic intervals.

11. The intraluminal guidewire of claim 9, wherein the guide wire includes a material selected from the group consisting of stainless steel, high strength precipitation hardened cobalt-chromium, cobalt-chromium-molybdenum alloy, or superelastic nickel-titanium.

12. The intraluminal guidewire of claim 9, wherein a ratio of a maximum cross-sectional diameter the relatively stiff intermediate core segment to a cross-sectional diameter of the relatively flexible intermediate core segment ranges from about 5% to about 75%.

* * * * *

UNITED STATES PATENT AND TRADEMARK OFFICE
CERTIFICATE OF CORRECTION

PATENT NO.    : 6,638,266 B1
DATED         : October 28, 2003
INVENTOR(S)   : W. Stan Wilson et al.

It is certified that error appears in the above-identified patent and that said Letters Patent is hereby corrected as shown below:

<u>Title page,</u>
Item [75], Inventors, add -- Peter J. D'Aquanni, Murrieta, CA (US) --.

Signed and Sealed this

Ninth Day of March, 2004

JON W. DUDAS
*Acting Director of the United States Patent and Trademark Office*